United States Patent [19]

Skuballa et al.

[11] 4,364,951
[45] Dec. 21, 1982

[54] PROSTACYCLINS AND USE AS MEDICINAL AGENTS

[75] Inventors: Werner Skuballa; Helmut Vorbrueggen; Olaf Loge; Peter Vischer; Bernd Radüchel, all of Berlin, Fed. Rep. of Germany

[73] Assignee: Schering Aktiengesellschaft, Berlin and Bergkamen, Fed. Rep. of Germany

[21] Appl. No.: 317,690

[22] Filed: Nov. 2, 1981

[30] Foreign Application Priority Data

Oct. 31, 1980 [DE] Fed. Rep. of Germany ....... 3041601

[51] Int. Cl.³ ................. A61K 31/557; C07D 307/935
[52] U.S. Cl. .................................... 424/263; 424/275; 424/285; 542/426; 542/429; 542/430; 544/224; 544/238; 544/336; 546/269; 548/204; 548/525; 549/60; 549/414; 549/465
[58] Field of Search .............. 260/346.22, 345.9; 542/426, 429, 430; 546/269; 549/60

[56] References Cited
U.S. PATENT DOCUMENTS 4,219,479 8/1980 Vorbrüggen et al. ......... 260/346.22

Primary Examiner—Henry R. Jiles
Assistant Examiner—Bernard Dentz
Attorney, Agent, or Firm—Millen & White

[57] ABSTRACT

Prostane derivatives of the formula

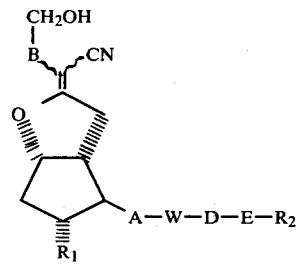

wherein
B is straight-chain or branched alkylene of 1–10 carbon atoms,
A is $-CH_2-CH_2-$, trans$-CH=CH-$, or $-C\equiv C-$;
W is hydroxymethylene or a

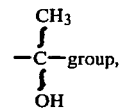

wherein the OH-group can be in the α- or β-position, and is optionally modified by replacement of the H atom with an ether or acyl group which is conventional for such replacements in prostaglandins and which is readily cleavable at physiological pH's;
D and E together are a direct bond or
D is straight-chain or branched alkylene of 1–10 carbon atoms, or, such an alkylene of 4–10 carbon atoms containing a double bond in the 2- or 3-position, all of which can optionally be substituted by fluorine, 1,2-methylene, 1,1-trimethylene, or methoxy;
E is oxygen, sulfur, $-C\equiv C-$ or a direct bond;
$R_2$ is $C_{1-10}$, $C_{2-10}$ alkenyl, each of which optionally is substituted phenyl, 1-naphthyl or 2-naphthyl, each of which is substituted as defined below; $C_{4-10}$ cycloalkyl optionally substituted by $C_{1-4}$ alkyl; phenyl, 1-naphthyl, or 2-naphthyl, each of which can optionally be substituted by 1–3 halogen atoms, a phenyl group, 1–3 alkyl groups each independently of 1–4 carbon atoms, or a chloromethyl, fluoromethyl, trifluoromethyl, carboxy, $C_1$-$C_4$-alkoxy, or hydroxy group, or an aromatic 5- or 6-membered heterocyclic ring having one hetero ring atom which is O, N, or S, the remaining atoms being carbon; and
$R_1$ is hydroxy optionally modified as for W above, have valuable vasodilating, anti-hypertensive, and bronchodilating pharmacological properties.

18 Claims, No Drawings

PROSTACYCLINS AND USE AS MEDICINAL AGENTS

BACKGROUND OF THE INVENTION

The present invention relates to novel prostacyclin derivatives, a process for their preparation, and their use as medicinal agents.

Prostacyclin ($PGI_2$), one of the primary factors in blood platelet aggregation, has a dilating effect on various blood vessels (Science 196, 1072). Thus, it could be considered as an agent for lowering blood pressure. However, $PGI_2$ does not possess the stability required for a medicine. The half-life of $PGI_2$ at physiological pH values and at room temperature is only a few minutes.

DOS [German Unexamined Laid-Open Application] No. 2,753,244 and its equivalent U.S. Pat. No. 4,219,479 describe prostacyclin derivatives stabilized by a nitrile group on the terminal ether double bond. However, it is still desired to have compounds whose properties are even better than those of such prostacyclins.

SUMMARY OF THE INVENTION

Accordingly, it is an object of this invention to provide new prostacyclins having improved properties and stability.

Upon further study of the specification and appended claims, further objects and advantages of this invention will become apparent to those skilled in the art.

These objects have been achieved by providing prostane derivatives of Formula I

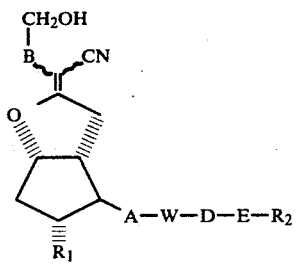

wherein
B is a straight-chain or branched alkylene group of 1–10 carbon atoms,
A is $-CH_2-CH_2-$, trans-$CH=CH-$, or $-C\equiv C-$,
W is a free or functionally modified hydroxymethylene group or a free or functionally modified

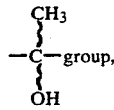

group, wherein the OH-group can be in the α- or β-position,
D and E jointly represent a direct bond or
D is a straight-chain or branched, saturated or unsaturated alkylene group of 1–10 carbon atoms, which can optionally be substituted by fluorine atoms, 1,2-methylene, 1,1-trimethylene or methoxy groups,
E is oxygen, sulfur, a $-C\equiv C-$ bond, or a direct bond,
$R_2$ is alkyl, alkenyl, cycloalkyl, optionally substituted aryl, or a heterocyclic group, and
$R_1$ is a free or functionally modified hydroxy group.

DETAILED DISCUSSION

It has been found that by replacing the 1-carboxy group in the 5-cyanoprostacyclins by a hydroxymethyl group, a prolonged duration of effectiveness and higher selectivity can be achieved.

The hydroxy groups $R_1$ and those in W can be conventionally functionally modified, for example by etherification or esterification. The free or modified hydroxy groups in W can be in the α- or β-position. Free hydroxy groups are preferred in both positions. Suitable modifying groups, e.g., ether and acyl residues are known to those skilled in the art and are groups which produce overall compounds which are physiologically active and which themselves are readily cleavable in vivo, e.g., at physiological pH's. Ether residues are preferred, such as, for example, tetrahydropyranyl, tetrahydrofuranyl, α-ethoxy-ethyl, trimethylsilyl, dimethyl-tert-butylsilyl, or tribenzylsilyl. Suitable acyl residues include $C_1-C_4$-alkanoyl residues, e.g., acetyl, propionyl, butyryl, or benzoyl.

Suitable groups $R_2$ include straight-chained or branched alkyl, alkenyl residues, preferably saturated residues, of 1–10, especially 1–7 carbon atoms. These can, optionally, be substituted by aryl groups, which latter can also be optionally substituted. Such aryl groups include those exemplified below for $R_2$ groups per se. Examples include methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

Suitable cycloalkyl groups $R_2$ have 4–10, preferably 5 or 6 ring carbon atoms. The rings can optionally be substituted by alkyl groups of 1–4 carbon atoms. Examples include: cyclopentyl, cyclohexyl, methylcyclohexyl, and adamantyl.

Examples of substituted or unsubstituted aryl groups $R_2$ include, for instance: phenyl, 1-napthyl, or 2-naphthyl, each of which can optionally be substituted by 1–3 halogen atoms, (e.g., F, Cl, Br), a phenyl group, 1–3 alkyl groups each independently of 1–4 carbon atoms, or a chloromethyl, fluoromethyl, trifluoromethyl, carboxy, $C_1-C_4$-alkoxy, or hydroxy group. Substitution in the 3- or 4- positions of the phenyl ring, for example by fluorine, chlorine, $C_1-C_4$-alkoxy, or trifluoromethyl, or in the 4-position by hydroxy, is preferred.

Suitable heterocyclic groups $R_2$ include heterocycles, of 5 and 6 ring members, among which those which are aromatic with one or two hetero atoms, e.g., nitrogen, oxygen, or sulfur are especially preferred. Examples include 2-furyl, 2-thienyl, 3-thienyl, 2-pyridyl, 3-pyridyl, 4-pyridyl, thiazolyl, pyrimidinyl, pyrazinyl, pyridazinyl, etc.

Suitable alkylene groups D include straight-chain or branched alkylene residues, optionally containing a double bond, but preferably saturated, of 1–10, especially 1–5 carbon atoms. These can optionally be substituted by 1–3 fluorine atoms or 1–3 $C_1-C_4$-alkyl groups, especially in the 1- or 2- position. Examples include: methylene, fluoromethylene, ethylene, 1,2-propylene, ethylethylene, trimethylene, tetramethylene, pentamethylene, 1-methyltetramethylene, 1-methyltrimethylene, 2-methyltrimethylene, 2-methyl-tetramethylene. If a double bond is present, it is in the alkylene residues of 4–10 carbon atoms and in the 2- or 3-position.

Preferred alkylene groups have 1–5 carbon atoms. Preferred alkylene groups are straight-chained alkylene residues of 1–10, especially 1–5, carbon atoms. Examples include: methylene, ethylene, trimethylene, tetramethylene, pentamethylene, etc.

The present invention furthermore relates to a process for preparing the prostane derivatives of this invention, comprising reacting a compound of Formula II

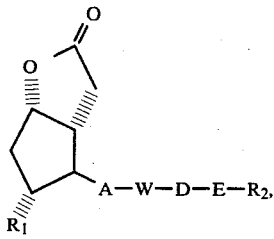

wherein $R_1$, $R_2$, A, W, D, E are as defined above, optionally, after blockage of any free hydroxy groups present, with a carbanion produced by reacting a nitrile of Formula III $$N \equiv C - CH_2 - B - CH_2OR_3 \qquad III$$

wherein
$R_3$ is a readily cleavable ether residue and
B is as defined above, with lithium diisopropylamide, and subjecting the resultant crude product to an acid treatment.

It is optionally possible, subsequently, and in any desired sequence, to separate isomers, liberate blocked hydroxy groups and/or esterify or etherify free hydroxy groups in the thus-obtained products of the process.

Suitable ether residues $R_3$ in the compounds of Formula III include the residues familiar to those skilled in the art. Preferred are ether residues which can readily split off, e.g., dimethyl-tert-butylsilyl, trimethylsilyl, tribenzylsilyl, tetrahydropyranyl, tetrahydrofuranyl, and α-ethoxyethyl, to name just a few.

The reaction of a compound of Formula II with the organometallic compound of Formula III (prepared conventionally from the corresponding nitrile with lithium diisopropylamide in ether-tetrahydrofuran mixtures in the presence of hexamethylphosphoric triamide) can be carried out conventionally at temperatures from 0° to −100° C., preferably at −60° to −78° C., in a solvent or solvent mixture suitable for organometallic reactions, preferably diethyl ether or tetrahydrofuran. To split off water, the crude product of the organometallic reaction is conventionally treated with a catalytic amount of an acid in a water-immiscible solvent, such as, for example, toluene, benzene, methylene chloride, chloroform, carbon tetrachloride, diethyl ether, etc., preferably in toluene or diethyl ether, at temperatures of from −20° to 100° C., preferably 0° to 30° C. Suitable acids include, for example, p-toluenesulfonic acid, sulfuric acid, hydrochloric acid, boron trifluoride, etc.

The functional modification of free OH-groups can be conducted according to methods known to one skilled in the art. To introduce the ether blocking groups, the reaction is conducted, for example, with dihydropyran in methylene chloride, benzene, or chloroform, using an acidic catalyst, e.g., $POCl_3$, p-toluenesulfonic acid, or anhydrous mineral acids. The dihydropyran is used in excess, preferably in two to ten times the theoretically required quantity. The reaction is normally completed at 0° to 30° C. after 15–30 minutes.

The introduction of acyl blocking groups is accomplished by conventionally reacting a compound of Formula I with a carboxylic acid derivative, e.g., an acid chloride, acid anhydride, and others, in the presence of a tertiary amine base, e.g., pyridine, dimethylaminopyridine, etc.

The liberation of a functionally modified OH-group to obtain the compounds of Formula I takes place according to conventional methods. For example, ether blocking groups can be split off in an aqueous solution of an organic acid, e.g., acetic acid, propionic acid, and others, or in an aqueous solution of an inorganic acid, e.g., hydrochloric acid. To improve solubility, a water-miscible inert organic solvent can be suitably added. Suitable organic solvents include for example, alcohols, e.g., methanol and ethanol, and ethers, such as dimethoxyethane, dioxane, and tetrahydrofuran. Tetrahydrofuran is preferably employed. The splitting-off step is preferably conducted at temperatures of 20° to 80° C.

The silyl ether blocking groups are split off, for example, with tetrabutylammonium fluoride or with KF in the presence of a crown ether. Examples of suitable solvents are tetrahydrofuran, diethyl ether, dioxane, methylene chloride, etc. The splitting-off reaction is preferably conducted at temperatures of 0° to 80° C.

The acyl groups can be saponified, for example, with alkali or alkaline earth carbonates or hydroxides in an alcohol or the aqueous solution of an alcohol. Suitable alcohols include aliphatic alcohols, e.g., methanol, ethanol, butanol, etc., preferably methanol. Worth mentioning as the alkali carbonates and hydroxides are potassium and sodium salts; but the potassium salts are preferred. Examples of suitable alkaline earth carbonates and hydroxides include calcium carbonate, calcium hydroxide, and barium carbonate. The reaction takes place at −10° to 70° C., preferably at 25° C.

The nitriles of Formula I produced in accordance with this process represent isomeric mixtures with respect to the double bond adjacent the cyano group; these mixtures can be separated by fully conventional separating methods, e.g., column chromatography or layer chromatography.

Nitriles of Formula III in this process can be produced conventionally, for example, from 1,5-alkanediols by selective silylation, tosylation, etc., and subsequent reaction with potassium cyanide.

The compounds of Formula II are known or can be conventionally prepared from known starting materials. See, e.g., DOS/German Unexamined Laid-open Application No. 2,845,770, and corresponding U.S. application, Ser. No. 086,506, filed on Oct. 19, 1979.

The compounds of this invention have vasodilating, blood-pressure-lowering, and bronchodilating activities. They are furthermore suitable for inhibiting thrombocyte aggregation and gastric acid secretion.

Consequently, the novel prostacyclin derivatives of Formula I are valuable pharmaceuticals. Moreover, with a similar spectrum of effectiveness, as compared with corresponding prostaglandins, they exhibit higher specificity and, above all, a substantially longer efficacy. As compared with $PGI_2$, they are distinguished by a higher stability.

The high tissue specificity of the novel prostaglandins can be demonstrated in a study of effects on smooth-muscle organs, e.g., on the guinea pig ileum or the isolated rabbit trachea, where a substantially lower stimulation is observed than in case of the administration of natural prostaglandins of the E, A, or F type.

The novel prostaglandin analogs of this invention possess properties which are typical for prostacyclins, e.g., they are useful in mammals, including humans, for lowering of peripheral arterial and coronary vascular resistance, inhibition of thrombocyte aggregation, dissolution of platelet thrombi, myocardial cytoprotection, lowering of systemic blood pressure without lowering at the same time the stroke volume and coronary blood flow; in treating stroke, prophylaxis and therapy of coronary heart disease, coronary thrombosis, cardiac infarction, peripheral arterial diseases, arteriosclerosis, and thrombosis; therapy for shock; inhibition of bronchoconstriction, inhibition of gastric acid secretion; and cytoprotection of gastric and intestinal mucosa; lowering of the pulmonary vascular resistance and pulmonary blood pressure, stimulation of kidney blood suffusion; usage in place of heparin or as an adjuvant in the dialysis of hemofiltration; preservation of blood plasma preserves, especially blood platelet preserves; inhibition of labor, treatment of gestational toxicosis (gestosis); increase of cerebral blood flow, etc.; they also have antiallergic properties. Furthermore, the novel prostaglandin analogs have antiproliferative properties.

The conventional prostacyclin compounds described above, are all potent in causing multiple biological responses even at low doses. Moreover, for many applications, these prostacyclins have an inconveniently short duration of biological activity. In striking contrast, the novel prostacyclin analogs of this invention are substantially more selective with regard to potency in causing prostacyclin-like biological responses, and have a substantially longer duration of biological activity. Accordingly, each of these novel prostacyclin analogs is surprisingly and unexpectedly more useful than one of the corresponding prostacyclins of the prior art for at least one of the pharmacological purposes indicated above, because it has a different and narrower spectrum of biological potency than the known compounds, and therefore is more specific in its activity and causes smaller and fewer undesired side effects than when the known compound is used for the same purpose. Moreover, because of its prolonged activity, fewer and smaller doses of the novel prostacyclin analog are frequently effective in attaining the desired result.

The general dose of the compounds of this invention is 1–1500 μg/kg/day, if administered to human patients. The unit dosage for the pharmaceutically acceptable vehicle is usually 0.01–100 mg.

Upon intravenous injection into nonanesthetized, hypertonic rats in doses of 5, 20, and 100 μg/kg body weight, the compounds of this invention show a stronger blood-pressure-lowering effect of a longer duration than do $PGE_2$ and $PGA_2$, without triggering diarrhea, as does $PGE_2$, or cardiac arrythmias, as does $PGA_2$.

When injected intravenously into anesthetized rabbits, the compounds of this invention show, as compared with $PGE_2$ and $PGA_2$, a stronger and considerably more prolonged lowering of the blood pressure without affecting other smooth-muscle organs or organ functions.

Sterile, injectable, aqueous or oily solutions are utilized for parenteral administration. Suitable for oral administration are, for example, tablets, dragees, or capsules.

The invention accordingly also relates to medicinal agents based on the compounds of Formula I and customary auxiliary agents and incipients.

The effective agents of this invention are to serve in conjunction with the auxiliary agents known and usual in galenic pharmacy, for example, for the production of blood-pressure-lowering agents.

The pharmacologically active compounds of formula I can be processed in accordance with conventional methods of galenic pharmacy to produce medicinal agents, especially for oral administration. Conventional excipients are pharmaceutically acceptable organic or inorganic carrier sustances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, which are sterile and injectable, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The administration of the compounds of this invention can be conducted in accordance with that for known prostacyclins such as Prostacyclin ($PGI_2$) except that advantage can be taken of their advantageous properties.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-Cyano-2-decarboxy-2-hydroxymethylprostacyclin 5.1 ml of diisopropylamide is combined at $-25°$ C. within 15 minutes with 23.5 ml of a 1.53-molar solution of butyllithium in hexane, and the mixture is stirred for 1 hour at $-25°$ C. The mixture is then combined with 6.3 ml of hexamethylphosphoric triamide and a solution of 8.2 g of 6-(dimethyl-tert.-butylsilyloxy)hexane nitrile in 5 ml of tetrahydrofuran is added dropwise to this mixture at −70° C. within 30 minutes. The mixture is agitated for 20 minutes at −70° C., a solution of 4.7 g of (1S,5R,6R,7R)-6-[(E)-(3S)-3-benzoyloxy-1-octenyl]-7-benzoyloxy-2-oxabicyclo[3.3.0]octan-3-one in 25 ml of ether and 30 ml of tetrahydrofuran is added thereto; the reaction mixture is stirred for 20 minutes at −70° C. and then acidified by pouring into a 10% citric acid solution to pH 5. The mixture is extracted three times with respectively 200 ml of ether, the organic phase is shaken twice with water, dried over sodium sulfate, and the residue of the evaporation is filtered with ethyl acetate over silica gel, thus obtaining 3.3 g of the reaction product of the organometallic reaction as the 11,15-dihydroxy compound.

To split off water, the reaction product from the aforedescribed reaction is dissolved in 150 ml of absolute diethyl ether, and 90 ml of a diluted ethereal boron trifluoride solution is added thereto (preparation: 0.9 ml of 45% boron trifluoride etherate solution is diluted with 81 ml of absolute ether), whereupon the mixture is stirred for 1 hour at room temperature under argon. The mixture is then poured on 5% sodium bicarbonate solution, washed neutral with water, dried over sodium sulfate, and evaporated under vacuum. Chromatography of the residue on silica gel yields initially 1.2 g of (5E)-5-cyano-2-decarboxy-2-(dimethyl-tert.-butyl-silyloxymethyl)prostacyclin and, as the more polar component, 0.98 g of the corresponding isomeric (5Z)-5-cyano-2-decarboxy-2-(dimethyl-tert.-butyloxymethyl)prostacyclin.

To effect silyl ether cleavage, the 1.2 g of the (5E)-configured compound is stirred for 18 hours at room temperature with 40 ml of a mixture of glacial acetic acid/water/tetrahydrofuran (65+35+10). The mixture is evaporated under vacuum and the residue chromatographed on silica gel. With methylene chloride/isopropanol (9+1), 740 mg of the title compound is obtained as a colorless oil.

IR: 3610, 3400 (broad), 2960, 2930, 2860, 2200, 1650, 1600, 970 cm$^{-1}$.

The starting material for the above title compound is prepared as follows:

1(a)

(1S,5R,6R,7R)-6-[(E)-(3S)-Benzoyloxy-1-octenyl]-7-benzoyloxy-2-oxabicyclo[3.3.0]octan-3-one At 0° C., 1.9 ml of benzoyl chloride is added to a solution of 3.1 g of (1S,5R,6R,7R)-6-[(E)-(3S)-3-hydroxy-1-octenyl]-7-benzoyloxy-2-oxabicyclo[3.3.0]octan-3-one in 15 ml of pyridine, and the mixture is agitated for 18 hours at room temperature. The mixture is then combined with 1.2 ml of water, agitated for 2 hours, diluted with 300 ml of ether, shaken once with 50 ml of water, twice with 10% sulfuric acid, once with 5% sodium bicarbonate solution, and three times with water. The mixture is dried over magnesium sulfate, evaporated under vacuum, and the residue is filtered over silica gel. With ether/hexane (8+2), 3.9 g of the dibenzoate is obtained as a colorless oil.

IR: 2960, 2925, 1770, 1715, 1602, 1585, 1270, 969 cm$^{-1}$.

1(b) 6-(Dimethyl-tert.-butylsilyloxy)hexane Nitrile

At ice bath temperature, 90.5 g of dimethyl-tert.-butylsilyl chloride is added to a solution of 62.5 g of 1,5-pentanediol and 102 g of imidazole in 100 ml of dimethylformamide, and the mixture is stirred for 16 hours at 0° C. The reaction mixture is then poured on 900 ml of water, extracted three times with respectively 500 ml of a mixture of hexane/ether (1+1), the organic extract is washed with water until neutral, and dried over magnesium sulfate. The product is concentrated under vacuum and the residue distilled under vacuum at 0.6 torr [mm Hg], thus obtaining, at 76°–80° C., 55 g of the monosilyl ether as a colorless liquid.

To form the tosylate, the product is dissolved in 185 ml of pyridine, and at ice bath temperature 74 g of p-toluenesulfonic acid chloride is added thereto. The mixture is agitated for 16 hours at room temperature, combined with 10 ml of water, agitated for 3 hours, diluted with 1.3 l of ether, shaken twice with 10% sulfuric acid, once with 5% sodium bicarbonate solution, and three times with water. The mixture is dried over magnesium sulfate and evaporated under vacuum, thus producing 79 g of the tosylate, which is dissolved in 185 ml of dimethyl sulfoxide, combined with 22 g of sodium cyanide, and stirred for 18 hours at 80° C. under argon. Subsequently the mixture is combined with 700 ml of water, extracted three times with respectively 400 ml of a mixture of ether/hexane (1+1), the organic extract is washed with water until neutral, and dried over magnesium sulfate. The product is concentrated under vacuum and the residue distilled under vacuum at 0.01 torr, thus obtaining at 75°–77° C. 43 g of the title compound as a colorless liquid.

IR: 2930, 2855, 2242, 1250, 1095, 830 cm$^{-1}$.

EXAMPLE 2

5-Cyano-2-decarboxy-2-hydroxymethyl-16-phenoxy-17,18,19,20-tetranorprostacyclin 2.95 ml of diisopropylamine is combined at −25° C. within 15 minutes with 13.95 ml of a 1.55-molar solution of butyllithium in hexane and agitated for 1 hour at −25° C. Subsequently, the mixture is combined with 3.7 ml of hexamethylphosphoric triamide and, at −70° C., a solution of 4.8 g of 6-(dimethyl-tert.-butylsilyloxy)-hexane nitrile in 4 ml of tetrahydrofuran is added dropwise to this mixture within 30 minutes. After 20 minutes, a solution of 3 g of (1S,5R,6R,7R)-6-[(E)-(3R)-3-benzoyloxy-4-phenoxy-1-butenyl]-7-benzoyloxy-2-oxabicyclo[3.3.0]octan-3-one in 15 ml of tetrahydrofuran and 15 ml of ether is added thereto, the mixture is stirred for 30 minutes and then acidified by pouring into a 10% citric acid solution to pH 5. The mixture is extracted with ether, the organic phase is washed neutral with water, dried over magnesium sulfate, and evaporated under vacuum. After chromatographing the residue on silica gel, 2.3 g of the reaction product of the organometallic reaction is obtained as the 11,15-diol.

To split off water, the reaction product from the above-described procedure is dissolved in 120 ml of absolute diethyl ether, 60 ml of a diluted ethereal boron trifluoride solution (preparation see Example 1) is added thereto, and the mixture is stirred for 1 hour at room temperature. Thereafter the mixture is poured on 5% sodium bicarbonate solution, washed neutral with water, dried over magnesium sulfate, and evaporated under vacuum. After chromatography of the residue on silica gel, the initial product is 0.9 g of (5E)-5-cyano-2-decarboxy-2-(dimethyl-tert.-butylsilyloxymethyl)-16-phenoxy-17,18,19,20-tetranorprostacyclin and as the more polar component, 0.78 g of the corresponding isomeric (5Z)-5-cyano-2-decarboxy-2-(dimethyl-tert.-butylsilyloxymethyl)-16-phenoxy-17,18,19,20-tetranorprostacyclin.

For the silyl ether cleavage, 0.9 g of the (5E)-configured compound is agitated at room temperature for 18 hours with 36 ml of a mixture of glacial acetic acid/water/tetrahydrofuran (65+35+10) and then evaporated under vacuum. By chromatography of the residue on silica gel, 620 mg of the title compound is obtained as a colorless oil with methylene chloride/isopropanol (9+1).

IR: 3600, 3400, 2930, 2860, 2198, 1650, 1599, 1586, 970 cm$^{-1}$.

2(a)
(1S,5R,6R,7R)-6-[(E)-(3R)-3-Benzoyloxy-4-phenoxy-1-butenyl]-7-benzoyloxy-2-oxabicyclo[3.3.0]octan-3-one Analogously to Example 1(a), 5 g of (1S,5R,6R,7R)-6-[(E)-(3R)-3-hydroxy-4-phenoxy-1-butenyl]-7-benzoyloxy-2-oxabicyclo[3.3.0]octan-3-one, 22 ml of pyridine, and 2.84 g of benzoyl chloride yield 6.1 g of the title compound as a colorless oil.

IR: 2940, 1770, 1714, 1599, 1586, 1270, 970 cm$^{-1}$.

EXAMPLE 3

5-Cyano-2-decarboxy-2-hydromethyl-16,16-dimethylprostacyclin

Analogously to Example 1, 2.1 g of (1S,5R,6R,7R)-6-[(E)-(3R)-3-benzoyloxy-4,4-dimethyl-1-octenyl]-7-benzoyloxy-2-oxabicyclo[3.3.0]octan-3-one results in 420 mg of the title compound as a colorless oil.

IR: 3600, 3400, 2962, 2935, 2860, 2200, 1650, 1600, 972 cm$^{-1}$.

The starting material for the above title compound is produced as follows:

3(a)
(1S,5R,6R,7R)-6-[(E)-(3R)-3-Benzoyloxy-4,4-dimethyl-1-octenyl]-7-benzoyloxy-2-oxabicyclo[3.3.0]octan-3-one In analogy to Example 1(a), 1.6 g of (1S,5R,6R,7R)-6-[(E)-(3R)-3-hydroxy-4,4-dimethyl-1-octenyl]-7-benzoyloxy-2-oxabicyclo[3.3.0]octan-3-one, 8 ml of pyridine, and 1 ml of benzoyl chloride yield 2 g of the dibenzoate as a colorless oil.

IR: 2962, 2930, 1770, 1715, 1600, 1588, 1270, 970 cm$^{-1}$.

EXAMPLE 4

5-Cyano-2-decarboxy-2-hydroxymethyl-15-methylprostacyclin

Analogously to Example 1, 0.5 g of (1S,5R,6R,7R)-6-[(E)-(3S)-3-hydroxy-3-methyl-1-octenyl]-7-benzoyloxy-2-oxabicyclo[3.3.0]octan-3-one and 850 mg of 6-dimethyl-tert.-butylsilyloxyhexane nitrile result in 85 mg of the title compound as a colorless oil.

IR: 3600, 3400 (broad), 2965, 2935, 2863, 2200, 1650, 1602, 972 cm$^{-1}$.

EXAMPLE 5

5-Cyano-2-decarboxy-2-hydroxymethyl-16-methylprostacyclin

In analogy to Example 1, 2.03 g of (1S,5R,6R,7R)-6-[(E)-(3S,4S)-3-benzoyloxy-4-methyl-1-octenyl]-7-benzoyloxy-2-oxabicyclo[3.3.0]octan-3-one results in 425 mg of the title compound as a colorless oil.

IR: 3610, 3420, 2960, 2935, 2863, 2200, 1650, 1600, 970 cm$^{-1}$.

The starting material for the above title compound is prepared as follows:

5(a)
(1S,5R,6R,7R)-6-[(E)-(3S,4RS)-3-Benzoyloxy-4-methyl-1-octenyl]-7-benzoyloxy-2-oxabicyclo[3.3.0]octan-3-one In analogy to Example 1(a), 1.7 g of (1S,5R,6R,7R)-6-[(E)-(3S,4RS)-3-hydroxy-4-methyl-1-octenyl]-7-benzoyloxy-2-oxabicyclo[3.3.0]octan-3-one, 8 ml of pyridine, and 1 ml of benzoyl chloride yield 2.06 g of the dibenzoate as a colorless oil.

IR: 2960, 2935, 1771, 1715, 1600, 1589, 1270, 972 cm$^{-1}$.

EXAMPLE 6

5-Cyano-2-decarboxy-2-hydroxymethyl-16-fluoroprostacyclin

In analogy to Example 1, 2 g of (1S,5R,6R,7R)-6-[(E)-(3R,4RS)-3-benzoyloxy-4-fluoro-1-octenyl]-7-benzoyloxy-2-oxabicyclo[3.3.0]octan-3-one results in 630 mg of the title compound in the form of an oil.

IR: 3630, 3410, 2958, 2936, 2860, 2202, 1650, 972 cm$^{-1}$.

The starting material for the above title compound is produced as follows:

6(a)
(1S,5R,6R,7R)-6-[(E)-(3R,4RS)-3-Benzoyloxy-4-fluoro-1-octenyl]-7-benzoyloxy-2-oxabicyclo[3.3.0]octan-3-one In analogy to Example 1(a), 2 g of (1S,5R,6R,7R)-6-[(E)-(3R,4RS)-3-hydroxy-4-fluoro-1-octenyl]-7-benzoyloxy-2-oxabicyclo[3.3.0]octan-3-one yields 2.3 g of the title compound as an oil.

IR: 2958, 2930, 2840, 1768, 1716, 1600, 1590, 1272, 976 cm$^{-1}$.

EXAMPLE 7

5-Cyano-2-decarboxy-2-hydroxymethyl-16-methyl-18,19-tetradehydroprostacyclin

In analogy to Example 1, 1 g of (1S,5R,6R,7R)-6-[(E)-(3S,4RS)-3-benzoyloxy-4-methyl-1-octen-6-inyl]-7-benzoyloxy-2-oxabicyclo[3.3.0]octan-3-one results in 280 mg of the title compound as an oil.

IR: 3605, 3430, 2960, 2936, 2200, 1650, 976 cm$^{-1}$.

The starting material for the above title compound is produced as follows:

7(a)
(1S,5R,6R,7R)-6-[(E)-(3S,4RS)-3-Benzoyloxy-4-methyl-1-octen-6-inyl]-7-benzoyloxy-2-oxabicyclo[3.3.0]octan-3-one Analogously to Example 1(a), 0.9 g of (1S,5R,6R,7R)-6-[(E)-(3S,4RS)-3-hydroxy-4-methyl-1-octen-6-inyl]-7-benzoyloxy-2-oxabicyclo[3.3.0]octan-3-one results in 1.04 g of the title compound as an oil.

IR: 2960, 2932, 2845, 1765, 1712, 1600, 1588, 1270, 972 cm$^{-1}$.

EXAMPLE 8

5-Cyano-2-decarboxy-2-hydroxymethyl-16-phenyl-17,18,19,20-tetranorprostacyclin Analogously to Example 1, 1 g of (1S,5R,6R,7R)-6-[(E)-(3S)-3-benzoyloxy-4-phenyl-1-butenyl]-7-benzoyloxy-2-oxabicyclo[3.3.0]octan-3-one results in 300 mg of the title compound as an oil.

IR: 3600, 3410, 2958, 2934, 2200, 1652, 1602, 974 cm$^{-1}$.

The starting material for the above title compound is prepared as follows:

8(a)
(1S,5R,6R,7R)-6-[(E)-(3S)-Benzoyloxy-4-phenyl-1-butenyl]-7-benzoyloxy-2-oxabicyclo[3.3.0]octan-3-one Analogously to Example 1(a), 1 g of (1S,5R,6R,7R)-6-[(E)-(3S)-3-hydroxy-4-phenyl-1-butenyl]-7-benzoyloxy-2-oxabicyclo[3.3.0]octan-3-one yields 1.25 g of the title compound as an oil.

IR: 2960, 2940, 2832, 1765, 1718, 1600, 1588, 1275, 974 cm$^{-1}$.

EXAMPLE 9

5-Cyano-2-decarboxy-2-hydroxymethyl-13,14-dihydro-16-phenoxy-17,18,19,20-tetranorprostacyclin Analogously to Example 1, 500 mg of (1S,5R,6R,7R)-6-[(3R)-3-benzoyloxy-4-phenoxybutyl]-7-benzoyloxy-2-oxabicyclo[3.3.0]octan-3-one results in 120 mg of the title compound as an oil.

IR: 3605, 3410, 2962, 2938, 2204, 1652, 1600, 1588 cm$^{-1}$.

The starting material for the above title compound is produced as follows:

9(a)
(1S,5R,6R,7R)-6-[(3R)-3-Benzoyloxy-4-phenoxybutyl]-7-benzoyloxy-2-oxabicyclo[3.3.0]octan-3-one In analogy to Example 1(a), 500 mg of (1S,5R,6R,7R)-6-[(3R)-3-hydroxy-4-phenoxybutyl]-7-benzoyloxy-2-oxabicyclo[3.3.0]octan-3-one yields 550 mg of the title compound as an oil.

IR: 2960, 2938, 1766, 1716, 1600, 1590, 1270 cm$^{-1}$.

EXAMPLE 10

5-Cyano-2-decarboxy-2-hydroxymethyl-16,20-dimethyl-18,19-tetradehydroprostacyclin In analogy to Example 1, 500 mg of (1S,5R,6R,7R)-6-[(3S)-3-benzoyloxy-4-methyl-1-nonen-6-inyl]-7-benzoyloxy-2-oxabicyclo[3.3.0]octan-3-one yields 100 mg of the title compound as an oil.

IR: 3600, 3420, 2956, 2934, 2840, 2202, 1650, 976 cm$^{-1}$.

The starting material for the above title compound is prepared as follows:

10(a)
(1S,5R,6R,7R)-6-[(3S)-3-Benzoyloxy-4-methyl-1-nonen-6-inyl]-7-benzoyloxy-2-oxabicyclo[3.3.0]octan-3-one In analogy to Example 1(a), 1 g of (1S,5R,6R,7R)-6-[(3S)-3-hydroxy-4-methyl-1-nonen-6-inyl]-7-benzoyloxy-2-oxabicyclo[3.3.0]octan-3-one results in 1.25 g of the title compound as an oil.

IR: 2960, 2935, 1770, 1716, 1600, 1588, 1274, 976 cm$^{-1}$.

EXAMPLE 11

(5Z)-5-Cyano-2-decarboxy-2-hydroxymethyl-16-phenoxy-17,18,19,20-tetranorprostacyclin A solution of 0.60 g of (5Z)-5-cyano-2-decarboxy-2-(dimethyl-tert.-butylsilyloxymethyl)-16-phenoxy-17,18,19,20-tetranorprostacyclin (see Example 2) is agitated for 18 hours with 30 ml of a mixture of glacial acetic acid/water/tetrahydrofuran (65+35+10) and then evaporated to dryness under vacuum. After chromatographing the residue on silica gel, eluting with methylene chloride/isopropanol (9+1), 0.41 g of the title compound is obtained as a colorless oil.

IR: 3605, 3400, 2930, 2865, 2210, 1650, 1600, 1588, 976 cm$^{-1}$.

EXAMPLE 12

(5Z)-5-Cyano-2-decarboxy-2-hydroxymethyl-16-methylprostacyclin

At $-25°$ C., 23.5 ml of a 1.53-molar solution of butyllithium in hexane is added to a solution of 5.1 ml of diisopropylamine; the mixture is combined with 6 ml of hexamethylphosphoric triamide and at $-70°$ C. a solution of 8.2 g of 6-(dimethyl-tert.-butylsilyloxy)hexane nitrile in 5 ml of tetrahydrofuran is added dropwise thereto. After 30 minutes, a solution of 4.85 g of (1S,5R,6R,7R)-6-[(E)-(3S,4RS)-3-benzoyloxy-4-methyl-1-octenyl]-7-benzoyloxy-2-oxabicyclo[3.3.0]-octan-3-one in 40 ml of ether and 40 ml of tetrahydrofuran is added dropwise to the reaction mixture; the latter is stirred for another 15 minutes at $-70°$ C., and the solution is poured on aqueous citric acid solution, thus obtaining a pH of 5. The mixture is extracted several times with ether, the organic phase is shaken with brine, dried over magnesium sulfate, filtered, and the evaporation residue is purified with ethyl acetate on silica gel, thus obtaining 3.6 g of an oily compound which, to split off water, is dissolved in 250 ml of ether and treated for 1 hour at 20° C. with 1 ml of 45% boron trifluoride etherate solution. Subsequently the mixture is poured on 5% sodium bicarbonate solution, the phases are separated, washed neutral with brine, dried over magnesium sulfate, and evaporated under vacuum. After chromatography of the residue on silica gel, the initial product is 1.3 g of (5E)-5-cyano-2-decarboxy-2-(dimethyl-tert.-butylsilyloxymethyl)-16-methylprostacycline and, as the more polar component, 1.05 g of the corresponding (5Z)-5-cyano-2-decarboxy-2-(dimethyl-tert.-butylsilyloxymethyl)-16-methylprostacyclin.

For silyl ether cleavage, 1.05 g of the (5Z)-configured compound is stirred for 18 hours at 20° C. with 35 ml of a mixture of glacial acetic acid/water/tetrahydrofuran (65/35/10), evaporated under vacuum, and the residue is chromatographed on silica gel, eluting with methylene chloride/isopropanol (9+1). Yield: 600 mg of the title compound as a colorless oil.

IR: 3610, 3410, 2958, 2936, 2862, 2200, 1650, 1601, 972 cm$^{-1}$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifica-

What is claimed is:

1. A prostane derivative of the formula

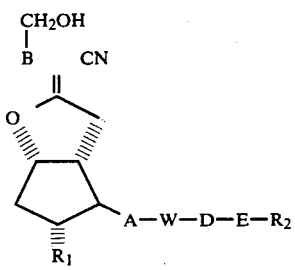

wherein

B is straight-chain or branched alkylene of 1–10 carbon atoms,

A is —CH$_2$—CH$_2$—, trans—CH=CH—, or —C≡C—;

W is hydroxymethylene or a

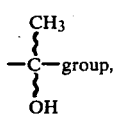

wherein the OH—group can be in the α-or β-position, and is optionally modified by replacement of the H atom with an ether or acyl group which is conventional for such replacements in prostaglandins and which is readily cleavable at physiological pH's;

D and E together are a direct bond or

D is straight-chain or branched alkylene of 1–10 carbon atoms or such alkylene of 4–10 carbon atoms containing a double bond in the 2- or 3-position, all of which can optionally be substituted by fluorine, 1,2-methylene, 1,1-trimethylene, or methoxy;

E is oxygen, sulfur, —C≡C— or a direct bond;

R$_2$ is C$_{1-10}$-alkyl or C$_{2-10}$ alkenyl each of which optionally is substituted by phenyl, 1-naphthyl or 2-naphthyl each of which is optionally substituted as defined below; C$_{4-10}$ cycloalkyl optionally substituted by C$_{1-4}$ alkyl; phenyl, 1-naphthyl, or 2-naphthyl, each of which is optionally substituted by 1–3 halogen atoms, a phenyl group, 1–3 alkyl groups each independently of 1–4 carbon atoms, or a chloromethyl, fluoromethyl, trifluoromethyl, carboxy, C$_1$–C$_4$-alkoxy, or hydroxy group; or an aromatic 5- or 6-membered heterocyclic ring having one hetero ring atom of O, N, or S, the remaining atoms being carbon; and R$_1$ is hydroxy optionally modified as described for W above.

2. 5-Cyano-2-decarboxy-2-hydroxymethylprostacyclin, a compound of claim 1.

3. 5-Cyano-2-decarboxy-2-hydroxymethyl-16-phenoxy-17,18,19,20-tetranorprostacyclin, a compound of claim 1.

4. 5-Cyano-2-decarboxy-2-hydroxymethyl-16,16-dimethylprostacyclin, a compound of claim 1.

5. 5-Cyano-2-decarboxy-2-hydroxymethyl-15-methylprostacyclin, a compound of claim 1.

6. 5-Cyano-2-decarboxy-2-hydroxymethyl-16-methylprostacyclin, a compound of claim 1.

7. 5-Cyano-2-decarboxy-2-hydroxymethyl-16-fluoroprostacyclin, a compound of claim 1.

8. 5-Cyano-2-decarboxy-2-hydroxymethyl-16-methyl-18,19-tetradehydroprostacyclin, a compound of claim 1.

9. 5-Cyano-2-decarboxy-2-hydroxymethyl-16-phenyl-17,18,19,20-tetranorprostacyclin, a compound of claim 1.

10. 5-Cyano-2-decarboxy-2-hydroxymethyl-13,14-dihydro-16-phenoxy-17,18,19,20-tetranorprostacyclin, a compound of claim 1.

11. 5-Cyano-2-decarboxy-2-hydroxymethyl-16,20-dimethyl-18,19-tetradehydroprostacyclin, a compound of claim 1.

12. (5Z)-5-Cyano-2-decarboxy-2-hydroxymethyl-16-phenoxy-17,18,19,20-tetranorprostacyclin, a compound of claim 1.

13. A compound of claim 1 wherein
W is hydroxymethylene or

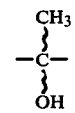

or such a group wherein the H atom of the OH group is replaced by tetrahydropyranyl, tetrahydrofuranyl, α-ethoxyethyl, trimethylsilyl, dimethyl-tert-butylsilyl, tribenzylsilyl or C$_{1-4}$-alkanoyl.

14. A compound of claim 1 wherein R$_2$ is C$_{1-7}$ alkyl, phenyl, 1-naphthyl or 2-naphthyl.

15. A compound of claim 1 wherein D is C$_{1-5}$ alkylene and B is C$_{1-5}$ alkylene.

16. A pharmaceutical composition comprising an antihypertensively effective amount of a compound of claim 1 and a pharmaceutically acceptable adjuvant.

17. A pharmaceutical composition of claim 16 wherein the amount of compound of claim 1 is 0.01 to 100 mg.

18. A method of lowering the blood pressure in a host in need of such treatment comprising administering an effective amount of a compound of claim 1 to the host.

* * * * *